US 6,685,321 B2

(12) United States Patent
Suzumura et al.

(10) Patent No.: US 6,685,321 B2
(45) Date of Patent: Feb. 3, 2004

(54) PERIMETER

(75) Inventors: Yoshikatsu Suzumura, Hamamatsu (JP); Takuya Hara, Hamamatsu (JP)

(73) Assignee: Kowa Company Ltd., Aichi (JP)

( * ) Notice: Subject to any disclaimer, the term of this patent is extended or adjusted under 35 U.S.C. 154(b) by 35 days.

(21) Appl. No.: 10/090,063

(22) Filed: Mar. 1, 2002

(65) Prior Publication Data

US 2002/0128558 A1 Sep. 12, 2002

(30) Foreign Application Priority Data

Mar. 2, 2001 (JP) ........................................ 2001-057577

(51) Int. Cl.[7] ................................................. A61B 3/02
(52) U.S. Cl. ......................................................... 351/224
(58) Field of Search ................................. 351/200, 201, 351/223, 224, 226, 237, 243, 244, 245

(56) References Cited

U.S. PATENT DOCUMENTS 5,108,170 A * 4/1992 Sugiyama .................... 351/226

* cited by examiner

*Primary Examiner*—George Manuel
(74) *Attorney, Agent, or Firm*—Adams & Wilks

(57) ABSTRACT

A perimeter has an optical projection system that projects a target spot on the inside surface of a visual field dome. The position at which the target spot is projected is controlled electronically. Input devices are used to input control information to control the target spot projection position and to record patient response information. A display means provides feedback display of the control information and patient response information, and also functions as an input screen via which the control and response information is input.

14 Claims, 4 Drawing Sheets

PRIOR ART

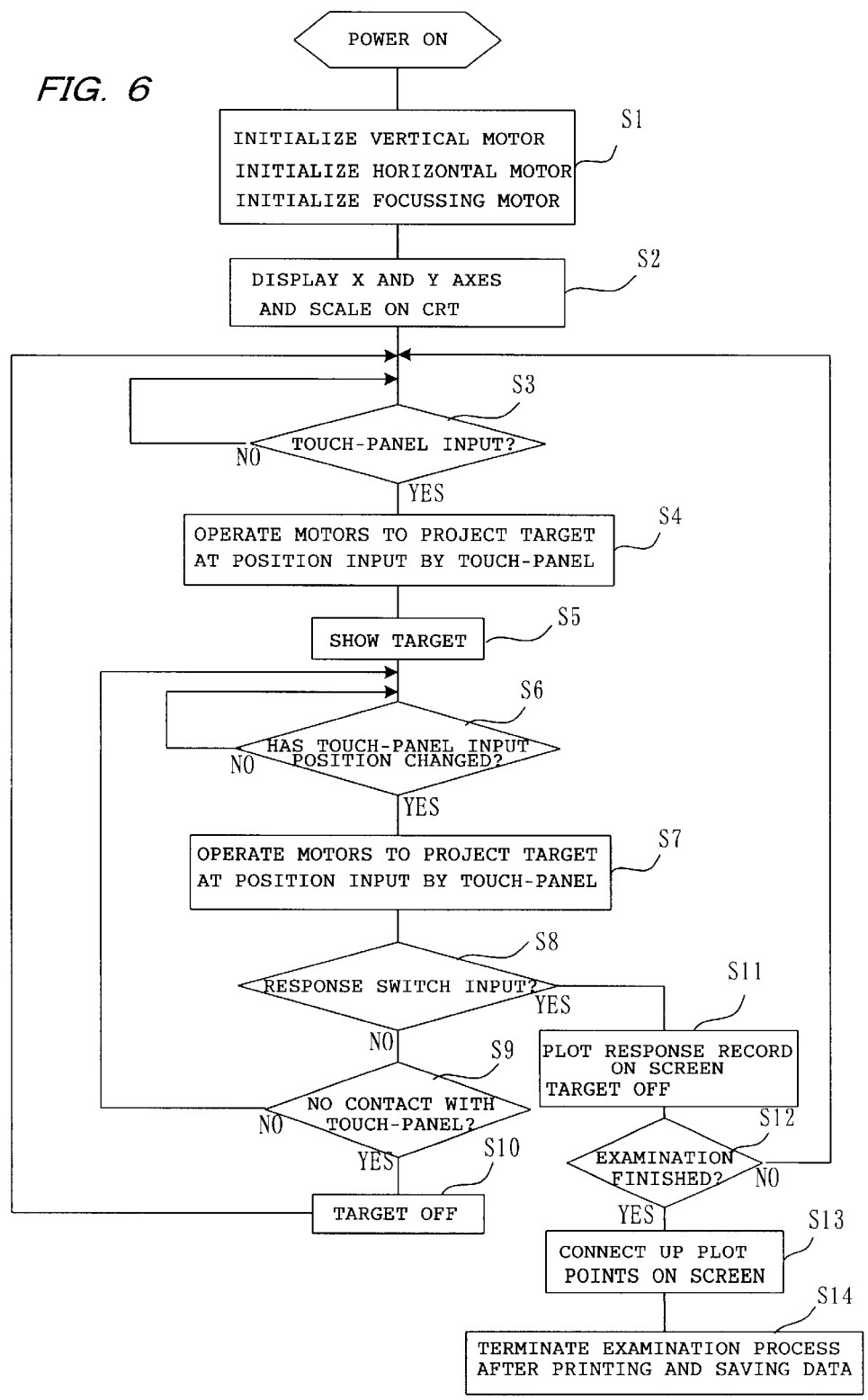

PERIMETER

BACKGROUND OF THE INVENTION

1. Field of the Invention

This invention relates to an oculo-perimetric device, otherwise known as a perimeter, and more particularly to a perimeter that projects a target spot onto the inside surface of a visual field dome and records the position of the projected target spot and a patient's responses relating to the visual recognition thereof.

2. Description of the Prior Art

Measuring a patient's visual field is an effective way of diagnosing some eye ailments. The Goldmann perimeter is extensively employed for such measurements. In a conventional Goldmann perimeter, a target spot is projected onto a hemispherical visual field dome of the perimeter, and an examiner manually adjusts the projection position of the spot by a means of a purely mechanical mechanism. The responses of the patient to the target spot are then recorded on a chart.

In addition to manual Goldmann perimeters, in recent years there has come into use automatic perimeters in which the control of the target is automated. In an automatic perimeter, the target projection mechanism is controlled in accordance with a predetermined program, or multiple LEDs or other such light sources are disposed which are lit in accordance with the program, and the patient operates a response button when given a suitable prompt.

A factor behind the emergence of the automated perimeter was that manual perimeters were difficult to use because the target had to be operated manually.

FIGS. 4 and 5 show the arrangement for a conventional manual Goldmann perimeter. In FIGS. 4 and 5, reference numeral 202 shows a visual field dome, in front of which a patient chin-rest 203 is positioned at the dome center. Over the dome 202 is a light source 211. To examine a patient's visual field, a projector 212 is used to project a target spot from the light source 211 at any point on the inside surface of the dome 202, and the patient's responses to the targets are recorded on a chart. The patient responds by pressing a push-button 213, which is located on the stand used to support the dome 202.

FIG. 5 is a rear view of the perimeter. As shown, at the center of the dome 202 there is a telescope 204 that is used to align the patient's eye with the perimeter and to monitor the examination sequences. The projector 212 is operated by a mechanical linkage comprising a pantograph 210a connected to the projector. At the end of the pantograph 210a, there is a handle 210. During the examination, a pen attached to the handle 210 records the positions of the target spot and the positions of the patient's responses on a printed paper 206 that is mounted at the back of the perimeter. An appropriate chart for isoptometry is printed on the recording pager for each system employed.

Because the target spot is operated and recorded by purely mechanical means in the case of a manual Goldmann perimeter, the measurement and recording operations require skill and experience. Moreover, during the examination the posture of the examiner is constrained, imposing a considerable burden on the examiner.

In an automatic perimeter the control of the target movement is automated according to a program. Although this simplifies the measurement operation, the use of a preprogrammed measurement sequence makes it impossible to change the measurement points to match a patient's particular situation, making it impossible to perform measurements with good efficiency. Another problem is the length of time it takes to perform the measurements. Manual Goldmann perimeters do not have the above problems of the automated perimeter, so the Goldmann perimeter had some advantages that were worth looking at.

It is therefore an object of the invention to solve such problems and provide a perimeter that has the advantages of both a manual Goldmann perimeter and an automatic perimeter, and can be manually operated with a degree of freedom and enables measurements to be performed readily and efficiently in accordance with the examiner's intentions.

SUMMARY OF THE INVENTION

In accordance with the present invention, the above object is attained by a perimeter that projects a target spot onto the inside surface of a visual field dome and records the position of the projected target spot and patient's responses relating to the visual recognition thereof, comprising an optical projection system for projecting the target spot on the inside surface of the visual field dome; control means including semi-automatic control means for electronically controlling the optical projection system to project the target spot onto only user-selected positions; input means used for entry of the user-selected positions for control of the projection position of the target spot by the control means and for recording of response information relating to the patient's response; and display means for displaying the user-selected positions control information and response information supplied via the input means, the display means having an input surface for entry of the user-selected positions and response information by the input means.

BRIEF DESCRIPTION OF THE DRAWINGS

These and other objects and advantages of the invention will be more apparent from the following description and drawings, in which:

FIG. 6 is a flow chart showing an examination sequence using a perimeter of the present invention.

DESCRIPTION OF THE PREFERRED EMBODIMENT

Embodiments of the invention will now be described with reference to the attached drawings.

The arrangement of a conventional Goldmann perimeter is used as the basis for the perimeter of the present invention, which is implemented as a semi-automatic perimeter that is as easy to use as an automated perimeter and enables measurements to be performed with flexibility and efficiency. This is accomplished by applying an electronic system to the operation of the Goldmann perimeter and using the electronic implementation to simulate the operational feel of a prior-art manual (mechanical) Goldmann perimeter.

Figure 1:
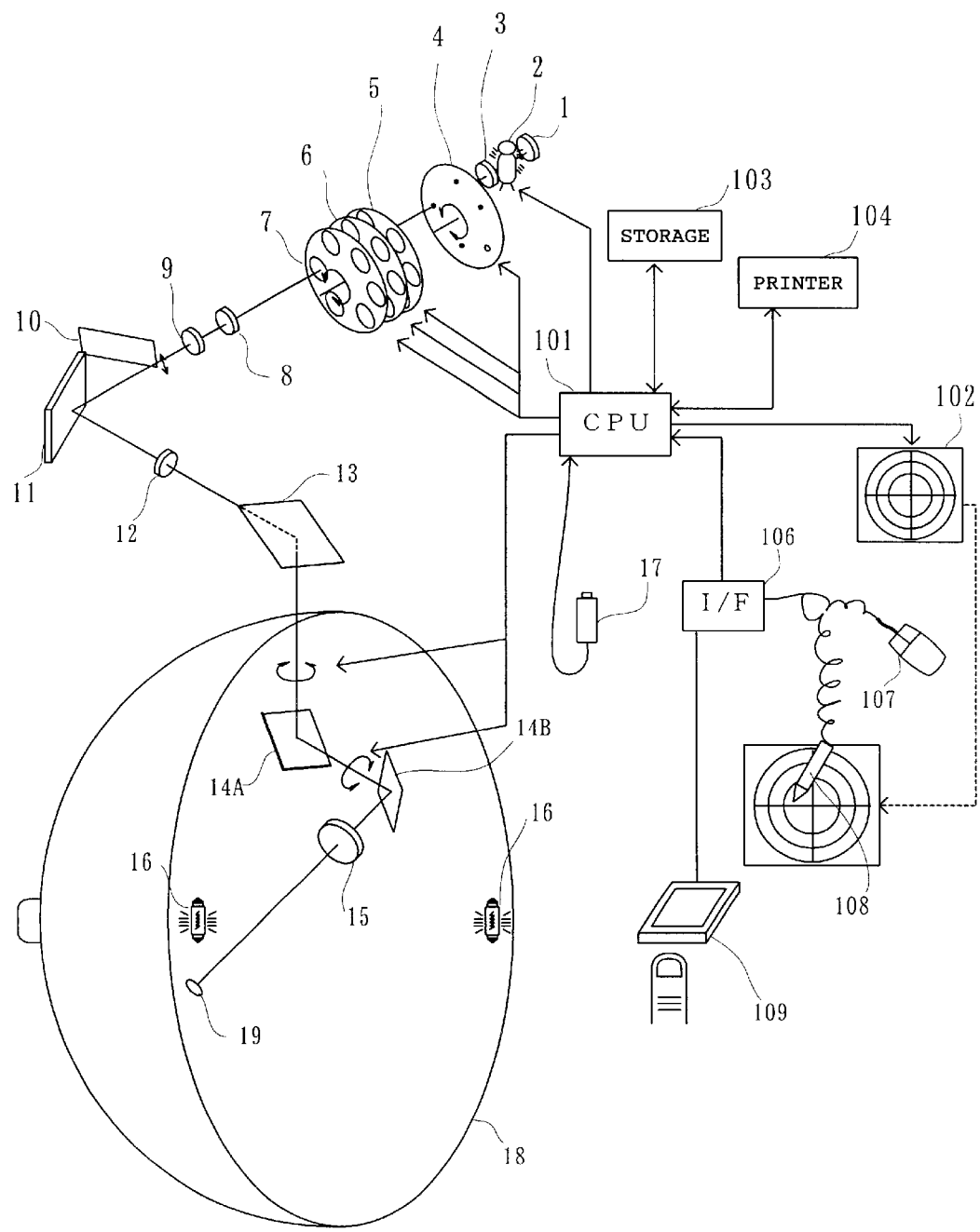
FIG. 1 is an illustrative view showing the arrangement of a perimeter according to the present invention.

FIG. 1 shows the structure of the perimeter of the invention. In FIG. 1, reference numeral 18 indicates a visual field dome. In the measurement procedure, the eye being examined is aligned with the center of the visual field dome 18 by means of a base and alignment mechanism (not shown). Background illumination lamps 16 are provided inside the visual field dome 18. The patient is told to look at a target 19 projected onto the inside surface of visual field dome 18. When the patient visually recognizes the target 19, he responds for the examiner by operating a response switch 17, or by giving a vocal response, or by any other suitable means.

Figure 4:
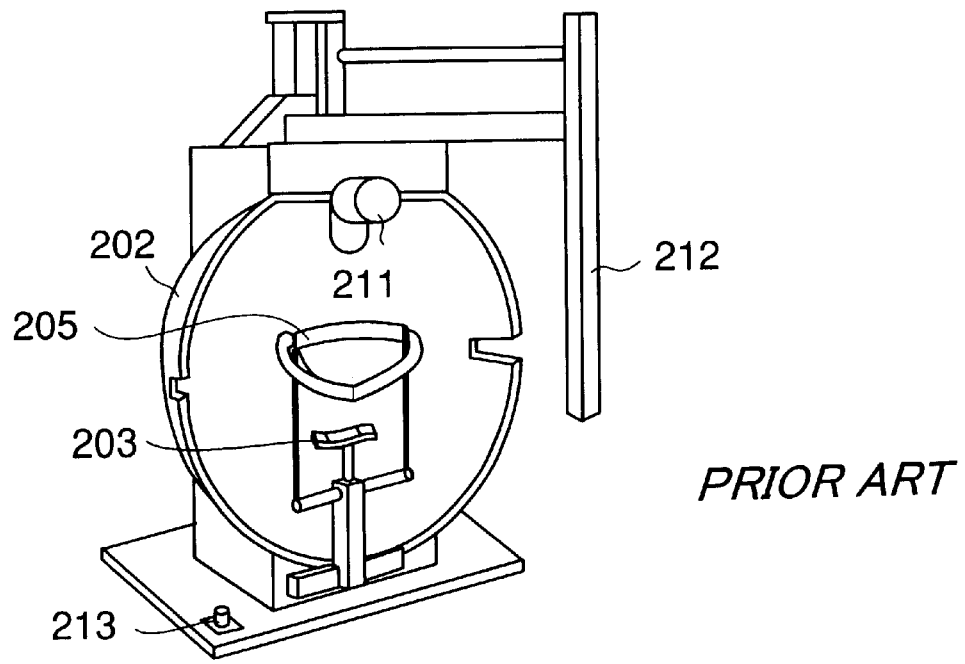
FIG. 4 is an illustrative view showing the front of a conventional mechanical (manual) Goldmann perimeter.
Figure 5:
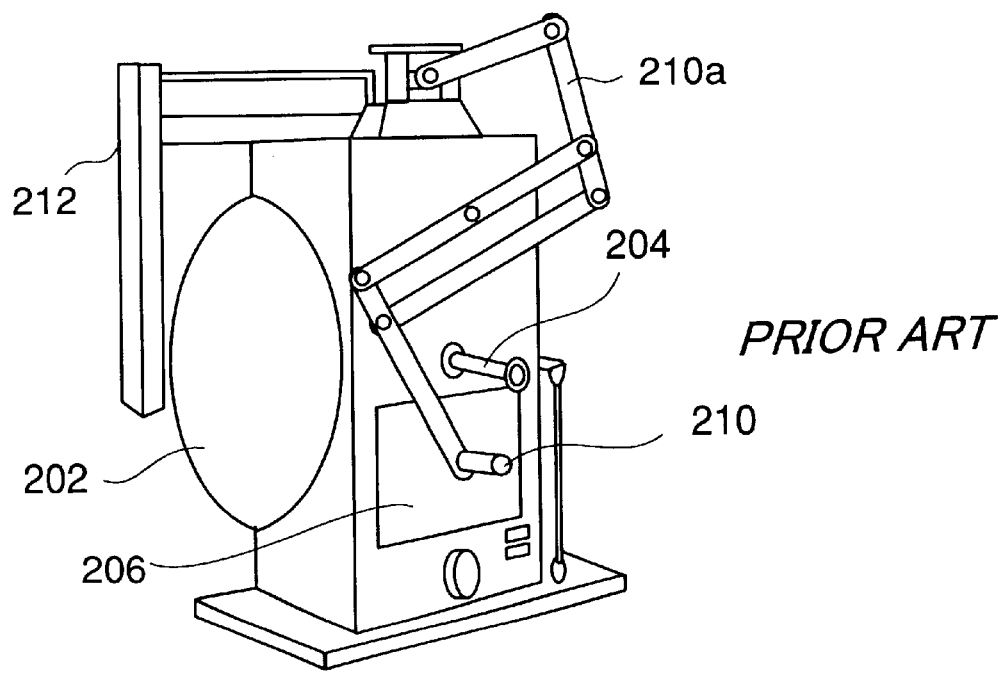
FIG. 5 is an illustrative view showing the rear of a conventional mechanical (manual) Goldmann perimeter.

In FIG. 1, an optical projection system comprising parts 1 to 15 is used to project the target 19. The optical system can, for example, be disposed inside the type of projector arm shown in FIGS. 4 and 5. Reference numeral 2 denotes a target projection lamp, behind which there is a reflecting mirror 1. Light from the lamp 2 passes through a condenser lens 3, a target plate 4 and turret filters 5 to 7, and falls incident on a relay lens 8. The target plate 4 is used to set the size of the target. For this, the target plate 4 is provided with a plurality of apertures, with the desired aperture being moved into the optical axis under the control of a CPU 101.

Of the turret filters 5 to 7, filter 5 is a color filter that selects the target color, and filters 6 and 7 are two different types of ND filter used to regulate the amount of light. From the relay lens 8, the light passes through a focusing lens 9 and a shutter 10 (aperture), deflected by a mirror 11, and the light passes through a relay lens 12 and is reflected by a mirror 13. In this embodiment, two mirrors, 14A and 14B, are provided to control the positioning of the projected target. For this, a drive means such as a motor (not shown) is used to rotate each mirror under the control of the CPU 101. Finally, the target is projected from a projector lens 15 onto the projection surface of the visual field dome 18.

The perimeter of this embodiment can be used as an automatic perimeter by controlling the target projection mechanism (1 to 15) under the control of the CPU 101 in accordance with the predetermined program, and visual field measurement can also be performed manually. That is, by applying operating means such as a display, mouse, tablet and the like to the operation system of a manual Goldmann perimeter, the manual operation system was implemented electronically. For this, the control system of the perimeter of the invention was arranged as follows.

The CPU 101 is connected to a display monitor 102 such as a CRT or liquid crystal display, an external storage unit 1–3 that uses floppy disks or MO (magneto-optical) media or the like, a printer 104, and the like. Via an I/O interface 16, the system is also provided with an input device or devices such as a mouse 107, a suitable pointing device 109, and a light-pen 108 used with the monitor.

Figure 3:
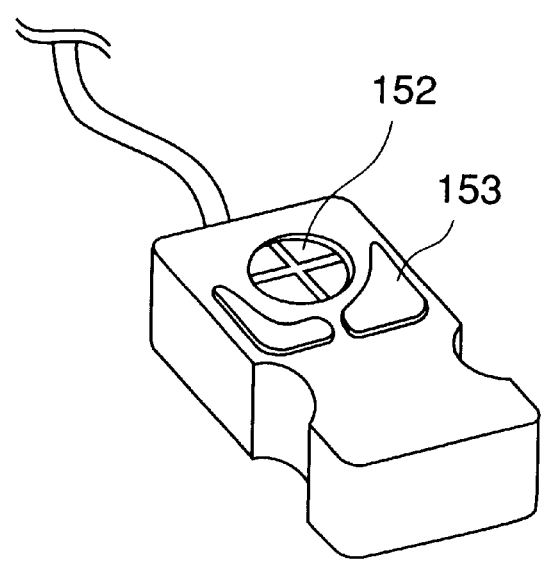
FIG. 3 is an schematic view showing an input device that can be used for a perimeter according to the invention.

The pointing device 109 can be a slide-pad operated by finger or special stylus, or a digitizer device as shown in FIG. 3. The digitizer device of FIG. 3 can be used on a digitizer pad on which is printed (or displayed) a conventional Goldmann perimeter recording chart pattern. A positioning aperture 152 can be used to check the position on the digitizer pad, and a click button 153 is used for command entry when the target spot position is determined or when the patient's responses are to be recorded. The current position of the pointing device 109 on the digitizer pad is output as coordinate data with the aid of coordinate detection systems such as mechanical, ball-based or optical systems.

Mouse, light-pen and pointing device systems are each used for coordinate entry, and it is not necessary to provide all of these devices. The examiner only needs to be provided with an operating feel that is as close as possible to that provided by using a recording chart with a conventional mechanical Goldmann perimeter.

Below, an example of a system using monitor 102 and light-pen 108 is described.

To implement automated perimeter operation, the target projection mechanism (1 to 15) is controlled via an interface and drive means such as motors and solenoids (not shown) under the control of the CPU 101 according to a predetermined program. This is the same as in the prior art, and further description thereof is therefore omitted.

When used as a (semi-) manual perimeter, the angles of the mirrors 14A and 14B are not adjusted by the examiner via a mechanical linkage, as in a conventional manual Goldmann perimeter. Instead, the light-pen 108 or pointing device 109 is used to make an indication on the recording chart pattern displayed on the monitor 102. If the mouse 107 or light-pen 108 is used as the input device, it produces coordinate signals on the basis of which a pointer is displayed on the monitor 102 to show the operation position. This enables the device button to be operated for command implementation. In the case of the digitizer device of FIG. 3, it is possible to use an arrangement in which the monitor 102 is used for display, and one in which the chart pattern is printed on the digitizer pad or shown on a display laid on the digitizer pad.

Figure 2:
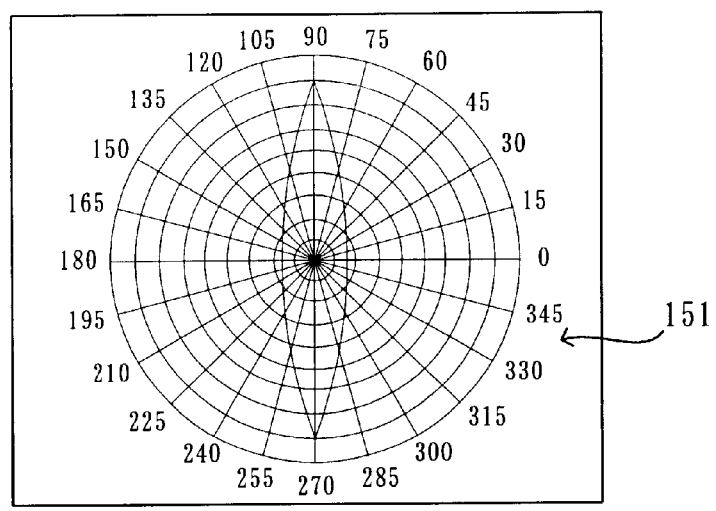
FIG. 2 is an illustrative view showing a recording chart displayed by the perimeter of this invention.

The chart pattern displayed on the monitor 102 is a recording chart pattern such as isoptometry suitable for any kind of perimetry system. A pattern 151 shown in FIG. 2 is an example. The pattern corresponds to the target projection surface of the visual field dome 18. The examiner uses the light-pen 108 or other input device for position entry on the pattern to control the projection position for the target spot and to record the patient's response position.

A suitable control system can be used to switch between inputting the target spot projection position and inputting the patient's response position. For example, a keyboard or foot-switch (not shown) can be used to switch between projection position input mode and response position input mode.

Based on the control and operating data that are input, the CPU 101 controls the target projection mechanism (1 to 15) and the target projection positioning.

FIG. 6 shows a flow chart of an examination sequence in the case of a perimeter according to the present invention used as a (semi-) manual perimeter. In this example, a touch-panel is provided on the monitor 102 to input the coordinate data. The mouse 107, light-pen 108 and pointing device 109 are not used, but can be readily replaced by the touch-panel in the following control operation.

With reference to FIG. 6, when the power is switched on, the motors are initialized in step S1. These are the motors used to drive the components such as the mirrors 14A and 14B for controlling the vertical and horizontal projection directions and the projector lens 15. In step S2, X and Y axes and scales are displayed on the monitor 102. The chart pattern of FIG. 2 can be used for this with the positions on the display and the touch-panel input coordinate system being associated beforehand with the actual visual field dome coordinate system.

In step S3, the system waits for input via the touch-panel on the monitor 102. When touch-panel input is received, the input coordinates are detected and the motors are energized in step S4 to project the target at the position thus input. The projection mechanism (1 to 15) is then controlled in step S5 to project the target spot at the coordinate position input on the touch-panel by the examiner.

Starting from step S6, the system enters a loop in which the target is projected at a plurality of points and the responses by the patient are input. In step S6, the touch-panel input is monitored to determine whether or not the input position has changed. If the input position has changed, the motors are energized in step S7 to project the target at the input position, as is the same with step S4. Thus, the examiner, while examining the patient, provides the patient with prompts, moving the target and requesting the patient to respond by using the response switch 17.

In step S8, it is determined whether or not there has been a patient input from the response switch 17. If there has been an input, the process moves to step S11. If there is no input, the process moves to step S9. In step S9, it is determined whether or not input via the touch-panel has stopped (that is, whether the examiner's finger or input stylus is off the touch-panel). If input has stopped, the target display is turned off in step S10 and the process goes back to step S3.

If there is a patient response, the process moves from step S8 to step S11, and the response is plotted on the screen of the monitor 102. Each such plot point corresponds to the target projection coordinates at the time of response switch operation. In addition to being plotted on-screen, the coordinate data corresponding to the response point are stored in memory for subsequent output processing and the like. In step S12, it is determined whether or not the examination has been finished. This can be done by, for example, determining the state of a Finish switch (not shown). If the examination is not finished, the process reverts to step S3, and the process of projecting and moving the target and recording responses is repeated.

If the examination is finished, an appropriate output process is effected via the monitor 102 in step S13. For example, a plurality of response positions can be connected on the monitor 102 to display a graph of the visual field range. In this step S13, the response position data can be displayed graphically on the monitor 102 in conformation with the examination system concerned by subjecting the data to computation appropriate for the examination system. In step S14, examination results are printed out by the printer 104. The output can be in the form of the screen dump in step S13, or can be in the form of a graph or table of target spot control and response positions. Along with this, the external storage unit 103 is used to store the examination data in a specified format.

Thus, the examiner just tracks the display on the monitor 102 using the touch-panel to readily set each of the target positions and obtain the patient's response at each point. Examination results are plotted on-screen and printed out automatically, freeing the examiner of the complex and onerous tasks of recording data on a chart, controlling the target positioning and plotting response positions that are required in the case of a conventional manual Goldmann perimeter. Patient prompts can be done arbitrarily, so that the examiner can use his own expertise and experience to decide the target projection sequence and positioning in accordance with the condition and state of the disease concerned, making it possible to expeditiously complete a full and proper examination.

As can be understood from the foregoing description and explanation, a perimeter according to the present invention can be used to project the target spot at the desired positions more easily than in the case of a conventional manual Goldmann perimeter in which the target spot position is controlled mechanically. In particular, the ability to concentrate the operating system in the touch-panel and monitor 102 and light-pen 108 (or the mouse 107 or pointing device 109 and the like) input devices makes it easy to operate during the examination procedure.

Operation is further facilitated by displaying the operation status on the monitor 102. For example, the current target projection position determined using the light-pen 108 (or mouse 107 or pointing device 109) can be displayed on the monitor 102 within the range of visual field that is shown in the form of a concentric recording chart pattern. When the response switch 17 is operated to signify a patient response, the position of the target spot at the time of the response can be acquired as a measurement result, and the response position can be displayed in a different color than the target projection position. It is also possible to automatically record the target spot position at the time of the response by the response switch or a spoken response by the patient.

If the light-pen 108 or the like is used, information relating to visual field measurement can be input in the form of handwritten characters. Handwritten input and character recognition of handwritten character input are known technologies, so further description thereof will be omitted. Also, menus required to control the operating modes of devices involved in visual field measurement can be displayed on the monitor 102 (or a digitizer pad or touch-panel or the like), enabling the examiner to use the light-pen 108 to make selections on the menus.

Instead of performing measurements in accordance with a fixed, preset program, measurement points and procedures can also be readily changed to match the needs of the patient or the condition of the patient's eye. This makes it possible to complete an examination with speed and efficiency, and, as compared to a conventional mechanical Goldmann perimeter, makes the examination less onerous and tiring for the examiner as well as the patient. This is accomplished by applying an electronic system to the operation of the Goldmann perimeter and using the electronic implementation to simulate the operational feel of a conventional manual (mechanical) Goldmann perimeter. This makes the perimeter as easy to use as an automatic perimeter, and enables examinations to be performed with good adaptability and efficiency.

Furthermore, the target projection mechanism (1 to 15) is not controlled by purely mechanical means; instead, the perimeter can utilize the target projection mechanism of an automatic perimeter, making it possible easily and at a low cost to configure as both an automatic perimeter and as a manual (semi-automatic) perimeter.

As described in the foregoing, the perimeter according to the present invention that projects a target spot onto the inside surface of a visual field dome and records the position of the projected target spot and patient's responses relating to the visual recognition thereof, comprises an optical projection system for projecting the target spot on the inside surface of the visual field dome; control means for electronically controlling a position at which the target spot is projected; input means used for entry of control information for control of the projection position of the target spot by the control means and for recording of response information relating to the patient's response; and display means for displaying the control information and response information supplied via the input means, said display means being adapted for use as an input surface for entry of the control and response information by the input means. In such an arrangement electronics is used to simulate the feel of a conventional manual (mechanical) Goldmann perimeter, making the perimeter as easy to use as an automatic perimeter, and enabling examinations to be performed with good adaptability and efficiency.

What is claimed is:

1. A perimeter that sequentially projects a target spot onto a plurality of user-selected positions located on an the inside surface of a visual field dome and records the positions of the projected target spot and a patient's responses relating to the visual recognition thereof, comprising:

an optical projection system for projecting the target spot onto the inside surface of the visual field dome;

control means for electronically controlling the optical projection system to sequentially project the target spot onto the plurality of user-selected positions;

input means for controlling the control means to enable sequential manual entry of the user-selected projection positions of the target spot and for recording of response information relating to the patient's responses; and display means for displaying the user-selected positions and response information supplied by the input means and having an input surface responsive to the input means for entry of the user-selected positions and response information;

wherein the control means includes semi-automatic control means for controlling the optical projection system during an examination to project the target snot onto only the user-selected positions on the inside surface of the visual field dome such that the target spot is projected to positions corresponding to the positions input on the display means using the input means.

2. A perimeter according to claim 1; wherein the input means is one of a mouse or a light-pen.

3. A perimeter according to claim 1; wherein the display means is one of a CRT display, a liquid crystal display, or a digitizer pad.

4. A perimeter according to claim 1; wherein the input surface is provided with a mechanical perimeter recording chart pattern, which is used by an examiner to determine the user-selected positions and response information.

5. A perimeter according to claim 1; wherein the control means further includes automatic control means for controlling the optical projection system according to a predetermined program to sequentially project the target spot onto pre-selected positions instead of the user-selected positions.

6. A perimeter according to claim 1; wherein the optical projection system comprises a projection lamp for producing light, a condenser lens interposed in an optical axis of the light to output a beam of condensed light, a movable target plate having a plurality of apertures locatable in the optical axis for setting a size of the light beam, a color filter for selecting a color of the light beam, one or more turret filters for regulating the intensity of the light beam, mirrors for reflecting the light beam onto the visual field dome, and drive means controlled by the control means for driving the mirrors to cause the light beam to be projected onto the user-selected positions on the inside surface of the visual field dome.

7. An oculo-perimetric device for performing a visual field examination, comprising: a visually observable target; a light projector for projecting light onto a surface of the target; an input device for manual input of user-selected projection positions; and semi-automatic control means for controlling the light projector to cause the light to be projected onto only the user-selected projection positions on the target surface during an examination.

8. An oculo-perimetric device according to claim 7; wherein the target comprises a visual field dome having a hemispheric inner surface viewable by a patient and onto which the light is projected.

9. An oculo-perimetric device according to claim 7; further comprising a display device for displaying the user-selected positions and response information supplied by the input device and having an input surface responsive to the input device for entry of the user-selected positions.

10. An oculo-perimetric device according to claim 9; wherein the display device is one of a CRT display, a liquid crystal display, and a digitizer pad.

11. An oculo-perimetric device according to claim 10; wherein the input surface is provided with a mechanical perimeter recording chart pattern which is used by an examiner to determine the user-selected positions.

12. An oculo-perimetric device according to claim 10; wherein the input device is one of a mouse and a light-pen.

13. An oculo-perimetric device according to claim 7; wherein the light projector comprises a projection lamp for producing light, a condenser lens interposed in an optical axis of the light to output a beam of condensed light, a movable target plate having a plurality of apertures locatable in the optical axis for setting a size of the light beam, a color filter for selecting a color of the light beam, one or more turret filters for regulating the intensity of the light beam, mirrors for reflecting the light beam onto the target, and drive means controlled by the control means for driving the mirrors to cause the light beam to be projected onto the user-selected positions on the target.

14. An oculo-perimetric device according to claim 7; further comprising automatic control means for controlling the light projector according to a program to sequentially project the light onto pre-selected positions instead of the user-selected positions.

* * * * *